United States Patent [19]

De Jage et al.

[11] 4,143,136
[45] Mar. 6, 1979

[54] METHOD OF CONTRACEPTION

[75] Inventors: Evert De Jage; Jacob De Visser, both of Oss, Netherlands

[73] Assignee: Akzona Incorporated, Asheville, N.C.

[21] Appl. No.: 852,215

[22] Filed: Nov. 17, 1977

[30] Foreign Application Priority Data

Nov. 20, 1976 [NL] Netherlands ........................ 7612955

[51] Int. Cl.² .............................................. A61K 31/56
[52] U.S. Cl. .................................... 424/240; 424/243;
260/112.5 LH
[58] Field of Search .............. 260/112.5 LH; 424/243, 424/240

[56] References Cited

U.S. PATENT DOCUMENTS

| | | | |
|---|---|---|---|
| 3,795,734 | 3/1974 | Rochefort | 424/243 |
| 3,892,723 | 7/1975 | McKinley et al. | 260/112.5 LH |
| 4,018,919 | 4/1977 | Black | 424/243 |

*Primary Examiner*—Elbert L. Roberts
*Attorney, Agent, or Firm*—Robert H. Falk; Charles A. Wendel; Francis W. Young

[57] ABSTRACT

A three-phase method of human female contraception wherein (1) starting on about the ninth to about the twelfth day of the female cycle (first cycle day being first menstruation day) an effective amount of at least one progestagenic substance is administered in daily or shorter intervals for about three to about six days followed at substantially similar intervals by (2) administration for about one to about three days starting from about the fourth to about the seventh day after the first phase of both an effective amount of the progestagenic substance(s), and a peptide possessing LHRF (Luteinizing Hormone Release Factor) activity, followed by (3) administration of an effective amount of the progestagenic substance(s) until the total time of the progestagenic substance administration with and without the LHRF compound is from about seven to about fifteen days. A contraceptive preparation or pack comprising a suitable number of dosage units ranging from about seven to about fifteen corresponding with the total time abovementioned, of which the first three to six dosage units contained as hormonal compound only an effective amount of a progestagenic substance, followed by one to three dosage units containing an effective amount of an orally LHRF active peptide in addition to the noted level of progestagenic substance, with the remaining dosage units again containing only the progestagenic substance at the level noted.

9 Claims, No Drawings

METHOD OF CONTRACEPTION

BACKGROUND OF THE INVENTION

1. Field of the Invention

The invention relates to the field of contraception and to the subfields of human female contraceptives and oral contraceptive devices.

2. Description of the Prior Art

The physiological processes occurring during the menstrual cycle of the woman are regulated by hormones from at least (1) the hypothalamus, (2) the hypophysis and (3) the ovary. In the first phase of the cycle, the follicular phase, the gonadotropic hormone FSH (Follicle Stimulating Hormone) is secreted by the hypophysis. FSH effects the development and maturation of one or more follicles in the ovary. In addition, oestrogen production increases, and under the oestrogenic influence, proliferation of the endometrium occurs.

In a second phase, follicle maturation is followed, about halfway through the cycle, by ovulation ond development of the corpus luteum from the ruptured follicle under an influence of another gonadotropic hormone, LH (Luteinizing Hormone). The secretion of the LH hormone is regulated by the hypothalamus, which in turn is again subject to ovarian influence.

Similarly under hormonal influence, the corpus luteum secretes progesterone during the luteal phase which follows ovulation; progesterone ensures that the proliferative endometrium changes into a secretory endometrium, suitable for implantation of a fertilized ovum. If the ovum is not fertilized during its journey through the Fallopian tubes to the uterus, the corpus luteum disappears after about 10 days, the progesterone level falls, and the endometrium is sloughed (menstruation).

Based on this hormonal process, a first generation (and now "classical") contraceptive method was developed about a decade ago based on the daily administration of a combination of (1) suitable oestrogenic and (2) suitable progestagenic substances over a period of a large fraction (usually 20 to 22 days) of the menstrual cycle. As a result of this so-called "combined treatment", ovulation is suppressed and an artificial monthly anovulatory bleeding is provoked.

This method is in general fairly reliable to prevent ovulation, but in addition to a number of unwanted incidental side effects such as nausea and weight increase, the method possesses a disadvantage that it brings about a deviation from the normal hormonal pattern.

A second method of contraception, developed at a later date, is the "continuous luteal supplementation" method, in which a suitable progestagenic substance is administered daily in low dosage throughout the entire cycle, and in the absence of an oestrogenic component.

The dosage used in this method is such that complete suppression of hypothalamic and hypophyseal function does not occur, so that the endogenous production of oestrogen is maintained, and inhibition of ovulation occurs sometimes, but often does not occur. In this method, the contraceptive properties are due to inhibition of the cyclical changes in the cervical mucus, as a result of which blockade of spermatozoa migration and inhibition of endometrial development occur. One of the major disadvantages of the continuous luteal supplementation method is that the constant administration of a progestagenic substance permits only a poor development of the endometrium, as a result of which irregular bleedings occur with all the associated objections.

It has already been suggested that these objections (nausea, weight increase, and irregular bleedings, inter alia) can be met by administering only a progestagenic substance, not throughout the entire cycle, but only for ten to fourteen days, beginning on day eight through ten of the cycle (see British patent specification No. 1,304,239), though in a dosage somewhat higher than that which is usual in the "continuous luteal supplementation" method, for example, 0.5–0.75 mg chlormadinone acetate. The change of inhibition of ovulation then increases, but the risk that ovulation occurs after ceasing administration also increases, so that contraceptive protection is then absent. For an example of another method, see U.S. Pat. No. 3,502,772 (1970).

An effective contraceptive method was needed, together with a suitably packaged pack with easily-administered components therefor which would prevent a deviation from the normal hormonal pattern while at the same time avoiding nausea, weight increase, and irregular bleedings, etc.

SUMMARY OF THE INVENTION

A new contraceptive method has now been found, which, starting on about the ninth to about the twelfth day of the cycle (first day of the cycle = first day of menstruation), a progestagenic substance is administered for a total of about seven to about fifteen days, with an additional simultaneous treatment comprising a peptide possessing LHRF (Luteinizing Hormone Releasing Factor) activity for about one to about three days, starting from about the fourth to about the seventh day after the commencement of the administration of said progestagenic substance. A peptide with LHRF activity may be further designated as an LHRF analogue. The progestagen is administered on daily or shorter intervals in an effective amount known to those skilled in the art, which is generally from about 0.01 mg to about 2.5 mg per day in daily doses (preferably in tablet or pill form). An LHRF analogue is preferably administered on daily or shorter intervals having about 0.1 mg to about 25 mg per unit in daily doses in a second stage to be described, and preferably in the same vehicle (pill or tablet, preferably) as the progestagenic substance. A new contraceptive preparation or pack is disclosed comprising a suitable container containing a predetermined number of dosage units ranging from about seven to about fifteen, of which the first three to six dosage units contained as hormonal compound only an effective amount (generally about 0.01 mg to 2.5 mg unit) of a suitable progestagenic substance, followed by one to three dosage units containing an orally LHRF active peptide, i.e., LHRF analogue (generally from about 0.1 to about 25 mg per unit of LHRF analogue), in addition to the noted level of progestagenic substances, with the remaining dosage units again containing only the progestagenic substances at the recited level. The pack comprises a suitable container (box, card, tube, etc.) having a predetermined number of regions (preferably at least 28) corresponding to at least a predetermined number of progestagenic substance-containing oral dosage units, which arrangement consists of:

(a) a first set of about three to about six dosage units, each having an effective amount of a suitable progestagenic substance;

(b) a second set of about one to about three dosage units, each having an effective amount of the suitable progestagenic substance together with an effective amount of a substance selected from the group consisting of peptides possessing LHRF; and (c) a third set of dosage units containing the progestagenic substance so that the total number of dosage units is from about seven to about fifteen;

wherein the first dosage unit of the first set is in a region of the suitable container which is suitably marked (by written date or instruction or otherwise known to those in the art) and indicates that said dosage is to be administered on a predetermined day from about the ninth to about the twelfth day after the onset of menstruation.

DESCRIPTION OF THE PREFERRED EMBODIMENTS

It is therefore possible to identify three distinct phases in the novel method: (1) an initial phase of about three to about six days (starting on about the ninth to about the twelfth day of the cycle), during which a progestagenic compound is administered, (2) a second phase of about one to about three days, during which an LHRF analogue is given in addition to the progestagen, and (3) subsequently a third phase during which again a progestagen is administered.

With this new method, administration of the active substance or, as the case may be, substances, may be by the enteral, parenteral or vaginal routes, while optionally the progestagen and the LHRF analogue may even be administered separately. Administration is usually by the enteral route, in particular oral (ingestion), sublingual or oromucosal. Furthermore, on days when it is to be taken, the LHRF analogue is preferably administered by incorporation into the pharmaceutical formulation used for administration of the progestagen. When reference is made to oral administration or dosage, it should be noted that this administration may also be sublingual or oromucosal, and that in such cases the amount of active agent needed to give a certain effect is generally less than that needed to produce the same effect after ingestion.

Within certain limits, the daily dosage of the progestational compound is tolerable. One of the factors governing the daily dosage is the potency and activity of the progestagen used, but it is in general from about 0.01 to about 2.5 mg, with the proviso that the amount of progestagen given during the first phase is so chosen that ovulation is suppressed. The daily dosage of orally active LHRF analogue during from about one to about three days commencing from about the fourth through the seventh day after administration of the progestational compound started, is also variable within certain limits, but is in general from about 0.1 to about 25 mg.

The invention also relates to a new contraceptive preparation or pack (i.e., "kit"), characterized by a suitable package form of a predetermined number of dosages (from about seven to about fifteen dosages) to be taken one every day of which the first (about three to about six) dosage units contain as hormonal compound a progestational substance in a dosage of about 0.01 to about 2.5 mg per unit, the following (about one to about three dosage) units contain in addition to the progestational substance at the level noted an orally active LHRF analogue in a dosage of about 0.1 to about 25 mg per unit and the remaining dosage units again contain a progestational substance at the level noted.

With proper use of the preparation and pack according to the invention, whereby the administration of hormones commences on about the ninth to about the twelfth day of the cycle, generally about the tenth day, and this administration is continued until about the sixteenth to about the twenty-fourth day of the cycle, excellent regulation of the cycle is obtained. The dosage scheme used leads to normal ovulation. At about the time of ovulation, while the penetrability of cervical mucus by spermatozoa would otherwise increase to a maximum, the administration of a progestational substance prevents penetration. The transition from the proliferative phase to the secretory phase of the endometrium occurs earlier employing the novel method, and is therefore no longer synchronized with ovulation. Hence, a surprisingly excellent contraceptive effect is obtained. The administration of the progestagenic substance and the endogenous progesterone production ensure that a cycle of normal duration and with normal menstruation is maintained.

In order to avoid mistakes resulting from forgetfulness by users, it is advantageous to use a "blank" or placebo on days where no hormonal component is administered. To this end, eight to eleven placebos for a normal cycle are added to the pack preceding the dosage units containing the progestagenic substance, and four to thirteen placebos are optionally added after the seven to fifteen dosage units containing the active substance.

The invention therefore also relates to a new contraceptive preparation and pack, which first contains in an order to be administered day-by-day commencing with the first day of the cycle a predetermined number of placebos (generally from about eight to about eleven), followed by a predetermined number of (about three to about six) dosage units having an effective amount of a progestagenic component, after which a predetermined amount of (about one to about three) dosage units containing both a progestagenic component and an orally active LHRF analogue are present, followed in turn by a predetermined number of dosage units with a progestagenic substance such that the total number of dosage units containing active agents is seven to fifteen, and optionally a further four to thirteen placebos. Generally, the placebos and dosage units are (1) identified in a one-to-one correspondence with numbers on the packaging form or with blanks with dates that the user can fill in and (2) total at least 28.

It is preferable that the placebos and progestagenic dosage units are rendered mutually distinctive by differences either in color and preferably in form.

Examples of suitable progestagenic substances, which are sometimes equivalently termed progestins, progestagens, progestational or gestagenic substances, include the following compounds:

17α-ethynyl-17β-hydroxy-$\Delta^4$-oestrene
17α-ethynyl-17β-hydroxy-$\Delta^5$-oestrene
11β-chloro-17α-ethynyl-17β-hydroxy-$\Delta^4$-oestrene
11-methylene-17α-ethynyl-17β-hydroxy-$\Delta^4$-oestrene
11-methylene-17α-ethynyl-17β-hydroxy-18-methyl-$\Delta^4$-oestrene
11β-methyl-17α-ethynyl-17β-hydroxy-$\Delta^4$-oestren-3-one
17α-ethynyl-17β-hydroxy-$\Delta^{4,9,11}$-oestratrien-3-one
17α-ethynyl-17β-hydroxy-18-methyl-$\Delta^4$-oestren-3-one
17α-vinyl-17β-hydroxy-$\alpha^{5(10)}$oestren-3-one
17α-ethynyl-17β-hydroxy-$\Delta^4$-oestren-3-one 17α-ethynyl-17β-acetoxy-Δ⁴-oestren-3-one
17α-ethynyl-17β-hydroxy-Δ⁵⁽¹⁰⁾-oestren-3-one
3β,17β-diacetoxy-17α-ethynyl-Δ⁴-oestrene
6α-methyl-17α-(1'propynyl)-17β-hydroxy-Δ⁴-androsten-3-one
17α-ethynyl-17β-acetoxy-Δ³,⁵-oestren-3-ol 3-cyclopentylether
6α-methyl-17α-acetoxy-progesterone
6-methyl-17α-acetoxy-Δ⁶progesterone
6-methyl-16-methylene-17α-acetoxy-Δ⁶-progesterone
6-chloro-17α-acetoxy-Δ⁶-progesterone
6-chloro-16-methylene-17α-acetoxy-Δ⁶-progesterone
16-methylene-17α-acetoxy-Δ⁶-progesterone
Δ⁴-9β,10α-pregnen-3,20-dione
Δ⁴,⁶-9β,10α-pregnadien-3,20-dione.

The progestagenic component may, of course, differ in the three aforesaid phases, also with respect to the amount present, and a mixture of two or more progestational components may also be used in one dosage unit. Usually, however, one and the same compound is used for all phases. The same is true of a LHRH-containing peptide or the LHRH analogue component.

In such cases where more than one dosage unit with LHRF is used, the same amount of LHRF is preferably also present in each dosage unit.

If the progestational compound is 17α-ethynyl-17β-hydroxy-Δ⁴-oestrene (lynestrenol), then it will preferably be used at a level of 0.5 to 2.5 mg per dosage unit; when, for example, 11-methylene-17α-ethynyl-17β-hydroxy-18-methylΔ⁴-oestrene is used, the preferred level is 0.05 to 0.25 mg per dosage unit. A routine amount of experimentation by one skilled in the art will obtain the optimum level of progestational compound needed.

If a second progestational compound is used in one or more of the phases, more or less of the second compound will be used per weight unit, depending on the relative activity of the first compound employed.

The following compounds, among many known to those in the art, may be cited as examples of suitable orally active peptides possessing LHRF activity (LHRF analogues):

(Des-Gly-NH$_2$-10)-LHRF-ethylamide
(D-Leu-6-desGly-NH$_2$-10)-LHRF-ethylamide
(D-Ala-6-desGly-NH$_2$-10)-LHRF-ethylamide
(D-Lys-6-desGly-NH$_2$-10)-LHRF-ethylamide
(D-Phe-6-desGly-NH$_2$-10)-LHRF-ethylamide
(D-Arg-6-desGly-NH$_2$-10)-LHRF-ethylamide
(D-Trp-6-desGly-NH$_2$-10)-LHRF-ethylamide
(D-Orn-6-desGly-NH$_2$-10)-LHRF-ethylamide
(ε-lauryl-D-Lys-6-desGly-NH$_2$-10)-LHRF-ethylamide
(δ-lauryl-D-Orn-6-desGly-NH$_2$-10)-LHRF-ethylamide
(Des-Gly-NH$_2$-10)-LHRF-(2,2,2-trifluoro)ethylamide
(t-Bu-D-Ser-6-desGly-NH$_2$-10)-LHRF-ethylamide
(Phe-5-D-Leu-6-desGly-NH$_2$-10)-LHRF-ethylamide
(D-Lys-6)-LHRF-polyglutaminate, sodium salt
(D-Phe-6)-LHRF
(D-Leu-6)-LHRF
(D-Tyr-6)-LHRF
(D-Ala-6)-LHRF
(D-Trp-6)-LHRF
(D-Lys-6)-LHRF
(D-Arg-6)-LHRF
(ε-diMe-D-Lys-6)-LHRF
(2-Me-Ala-6)-LHRF
(Des-Gly-NH$_2$-10)-LHRF-propylamide
(D-Trp-6)-LHRF-ethyl amide.

It has already been noted that the method of administration is not restricted to the oral form, although this is the most preferable. If an oral form is employed, the active compound or compounds, after mixing with the usual pharmaceutically acceptable excipients such as lubricants, binding agents, fillers or diluents and dyestuffs, may be processed to give a pharmaceutical formulation such as a tablet, pill, capsule, dragee or paper.

The placebos may be manufactured from the same excipients, but naturally without the addition of hormonal components.

Indications of days are preferably given on the pack according to the invention, showing at which point in the cycle the pharmaceutical formulation corresponding to the indicated day must be taken. The suitable package form may be any of a variety of a tube, a box, a card, etc., as known to those skilled in the art.

In the case of a box, which may be round, rectangular or another shape, the pharmaceutical units are enclosed separately in a grid or along the periphery of the box, while the box is provided with an optionally adjustable series of day-indications corresponding to the days on which each of the groups of tablets must be taken. If boxes are used, each pharmaceutical unit is loaded in its own individual region or holder bearing an adjustable or non-adjustable series or day-of-the-month indications showing when the units (tablets, pills, etc.) are to be taken.

Another suitable practical type of packaging consists of placing the pharmaceutical forms on a card of some suitable material, preferably a presspack, for example, a press-through strip of aluminum foil, whereby the day-instructions have been printed on the card.

Although the invention has been described with reference to specific embodiments above, numerous variations and modifications will become evident to those skilled in the art, without departing from the scope and spirit of the invention as described above and defined in the appended claims, and as shown in the following Examples:

EXAMPLE I

A. Placebo—Type A

| Potato starch | 19 mg |
| --- | --- |
| Stearic acid | 1 mg |
| Talc | 4 mg |
| Sunset yellow FCF | 0.025 mg |
| Lactose | up to 100 mg |

B. Placebo—Type B

| Gelatine | 3 mg |
| --- | --- |
| Talc | 8 mg |
| Magnesium stearate | 3.5 mg |
| Lactose | up to 100 mg |

EXAMPLE II

The following preparations may be used during the first (and third) progestational phases:

A. Dosage Unit—Type A

| | |
|---|---|
| 17 α-ethynyl-17β-hydroxy-Δ⁴-oestrene | 0.75 mg |
| Potato starch | 18.5 mg |
| Glycerol (100%) | 1.9 mg |
| Magnesium stearate | 1 mg |
| Talc | 4 mg |
| α-tocopherol | 0.2 mg |
| Sunset yellow FCF | 0.025 mg |
| Lactose | up to 100 mg |

B. Dosage Unit—Type B

Corresponding to the composition given in Example II(A), but in which the progestational component has been replaced by:

| | | |
|---|---|---|
| (a) | 11-methylene-17α-ethynyl-17β-hydroxy-18-methyl-Δ⁴-oestrene | 0.06 mg |
| (b) | 6-methyl-17α-acetoxy-Δ⁶-19-nor-progesterone | 1.0 mg |
| or (c) | 11β-chloro-17α-ethynyl-17β-hydroxy-Δ⁴-oestrene | 0.5 mg |
| (d) | 17α-ethynyl-17β-hydroxy-18-methyl-Δ⁴-oestren-3-one | 0.1 mg |

EXAMPLE III

The following preparations may be used during the second progestational and LHRF-containing phase:

A. Dosage Unit—Type A

With the composition specified in II(A) or (B), but having additionally a certain amount of an LHRF analogue, to wit:

| | |
|---|---|
| (D-Ala-6-desGly-NH-10)-LHRF-ethylamide | 0.25 mg |
| (D-Leu-6-desGly-NH₂-10)-LHRF-ethylamide | 0.5 mg |
| (D-Trp-6)-LHRF-ethylamide | 1.0 mg |
| or (t-Bu-D-Ser-6-desGly-NH₂-10)-LHRF-ethylamide | 0.5 mg |

B. Dosage Unit—Type B

A progestational substance as identified in Examples II(A) or II(B) with an LHRF analogue as identified in Example III(A) is employed with the following:

| | |
|---|---|
| Progestational substance | as specified in III A. |
| LHRF-analogue | as specified in III A. |
| Corn starch | 29.2 mg |
| Talc | 4.8 mg |
| Magnesium stearate | 0.6 mg |
| Amaranth | 0.046 mg |
| Lactose | up to 100 mg |

What is claimed is:

1. A method of human female contraception comprising:
   administering to a human female a contraceptively effective amount of at least one progestagenic compound at daily or shorter intervals for about three to about six days commencing from about the ninth to about the twelfth day after the onset of menstruation in said human female;
   administering in a second stage thereafter to said human female a contraceptively effective amount of at least one progestagenic compound and a contraceptively effective amount of a peptide having LHRF activity at daily or shorter intervals for about one to about three days; and
   administering in a third stage thereafter to said human female a contraceptively effective amount of at least one progestagenic compound at daily or shorter intervals until a progestagenic compound has been administered for a total period of about seven to about fifteen days.

2. The method of claim 1, wherein a placebo is administered on daily or shorter intervals each day that the progestative compound is not administered.

3. The method of claim 1, wherein the progestagenic compound is administered in an amount of from about 0.01 to about 2.5 mg daily.

4. The method of claim 1, wherein said peptide having LHRF activity is administered in the second phase from about 0.1 to about 25 mg daily.

5. The method of claim 1, wherein the progestagenic compound employed is selected from the group consisting of 17α-ethynyl-17β-hydroxy-Δ⁴-oestrene; 11-methylene-17α-ethynyl-17β-hydroxy-18-methyl-Δ⁴-oestrene; 6-methyl-17α-acetoxy-Δ⁶-19-nor-progesterone; 11β-chloro-17α-ethynyl-17β-hydroxy-Δ⁴-oestrene, and 17α-ethynyl-17β-hydroxy-18-methyl-Δ⁴-oestrene-3-one.

6. The method of claim 5, wherein the progestagenic compound employed is 17α-ethynyl-17β-hydroxy-Δ⁴-oestrene (lynestrenol) at an amount of from about 0.5 to about 2.5 mg daily.

7. The method of claim 1 wherein the peptide having LHRF activity is selected from the group consisting of (D-Ala-6-desGly-NH₂-10)-LHRF-ethylamide, (D-Leu-6-desGly-NH₂-10)-LHRF-ethylamide, (D-Trp-6)-LHRF-ethylamide, and (t-Bu-D-Ser-6-desGly-NH₂-10)-LHRF-ethylamide.

8. A pack for the prevention of conception in females comprising:
   a suitable container having at least a predetermined number of regions corresponding to a predetermined number of progestagenic compound-containing oral dosage units, each unit to be administered daily, in a predetermined consecutive arrangement, which arrangment comprises:
   (a) a first set of about three to about six dosage units, each having an effective amount of a progestagenic compound; followed by
   (b) a second set of about one to about three dosage units, each having an effective amount of the progestagenic compound together with an effective amount of a peptide having LHRF activity; and
   (c) a third set of dosage units containing the progestagenic compound so that the total number of dosage units is from about seven to about fifteen;
   wherein the first dosage unit of the first set is in a region whose periphery indicates that said dosage is to be administered on a predetermined day from about the ninth to about the twelfth day after the onset of menstruation.

9. A pack as described in claim 8 having at least twenty-eight regions wherein each region contains either a placebo or progestagenic compound-containing dosage unit.

* * * * *